United States Patent [19]

Affeldt, Jr. et al.

[11] Patent Number: 5,152,401
[45] Date of Patent: Oct. 6, 1992

[54] AGRICULTURAL COMMODITY CONDITION MEASUREMENT

[75] Inventors: Henry A. Affeldt, Jr., Columbia; Judith A. Abbott, Beltsville, both of Md.

[73] Assignee: The United States of America as representd by the Secretary of Agriculture, Washington, D.C.

[21] Appl. No.: 421,028

[22] Filed: Oct. 13, 1989

[51] Int. Cl.$^5$ .................. B07C 5/34; G01H 13/00; G01N 29/06
[52] U.S. Cl. .................. 209/556; 73/12; 73/579; 209/590; 209/599; 209/931
[58] Field of Search .............. 209/555, 556, 558, 576, 209/590, 599, 931; 73/12, 579

[56] References Cited

U.S. PATENT DOCUMENTS

| | | | |
|---|---|---|---|
| 2,277,037 | 3/1942 | Clark et al. | 209/599 X |
| 2,635,746 | 4/1953 | Gordon | 209/590 X |
| 3,003,628 | 10/1961 | Diamond et al. | 209/599 |
| 3,029,943 | 4/1962 | Diamond et al. | 209/590 |
| 3,438,493 | 4/1969 | Goble | 209/590 |
| 3,580,056 | 5/1971 | Warner | 73/579 |
| 4,519,245 | 5/1985 | Evans | 73/579 |
| 4,884,696 | 12/1989 | Peleg | 209/599 X |

FOREIGN PATENT DOCUMENTS

| | | | |
|---|---|---|---|
| 1-217255 | 8/1989 | Japan | 209/599 |
| 0266230 | 7/1970 | U.S.S.R. | 209/590 |

OTHER PUBLICATIONS

Abbott, J. A., G. S. Bachman, N. F. Childers, J. V. Fitzgerald, and F. J. Matusik, 1968, Sonic Techniques for Measuring Textrue of Fruits and Vegetables, Food Technol. 22(5):101–112.

E. E. Finney et al., 1978, "Methods for Testing the Dynamic ... ", J. Food Quality 2:55–74.

E. E. Finney, Jr., 1972, "Vibration Techniques for Testing ... ", J. Texture Studies, 3:263–283.

Finney, E. E., Jr., 1970, Mechanical Resonance with Red Delicious Apples and Its Relation to Fruit Texture, Trans. ASAE 177–180.

Bower, D. R. and R. P. Rohrbech, 1976, Application of Vibrational Sorting to Blueberry Firmness Separation, Trans. ASAE 185–191.

Finney, E. E., Jr., 1971, Vibration Techniques for Testing Fruit, ASAE Paper 71–802.

Abbott, J. A., N. F. Childers, G. S. Bachman, J. V. Fitzgerald, and F. J. Matusik, 1968, Acoustic Vibration for Detecting Textural Quality of Apples, Proc. Amer. Soc, Hort. Sci. 93:725–737.

Finney, E. E., I. Ben-Gera and D. R. Massie, 1968, An Objective Evaluation of Changes in Firmness of Ripening Bananas Using a Sonic Technique, J. of Food Science 32(6):642–646.

Finney, E. E., Abbott, J. A. Watada, A. E. and D. R. Massie, 1978, Nondestructive Sonic Resonance and the Texture of Apples, J. Amer. Soc. Hort. Sci. 103(2):158–162.

Hard, M. M. and A. R. Hard, 1976, Static and Dynamic Measures for Fresh Apple Texture, J. Amer. Soc. Hort. Sci. 101(4):361–367.

Aylsworth, Jean, "High-Tech Packing" in American Fruit Grower, Sep. 1988, pp. 9 and 10.

*Primary Examiner*—Michael S. Huppert
*Assistant Examiner*—Edward M. Wacyra
*Attorney, Agent, or Firm*—M. Howard Silverstein; J. D. Fado; Janelle S. Graeter

[57] ABSTRACT

The instant invention pertains to ascertaining the condition (i.e. texture, maturity and extent of damage (if any)) of an agricultural commodity by: (a) inputting band-limited vibrations (i.e. limited to a specific frequency band); (b) sensing vibrational characteristics (e.g. energy, resonance, absorption frequency characteristics) resulting from the input vibrations, and; (c) analyzing the vibrational characteristics.

20 Claims, 8 Drawing Sheets

AGRICULTURAL COMMODITY CONDITION MEASUREMENT

FIELD OF THE INVENTION

The present invention relates to determination of the condition of an agricultural commodity (AC) e.g. fruits and vegetables, by inputting band-limited vibrations, sensing vibrational characteristics of the commodity resulting from the input vibrations, and analysis of the vibrational characteristics.

BACKGROUND OF THE INVENTION

It is known in the art to vibrate objects at specific frequencies to measure mechanical factors such as rigidity.

It is also known that vibration of fruit can indicate a state of ripeness or non-ripeness. See for example U.S. Pat. No. 2,277,037.

It is also known that solid fruit transmits higher frequency vibrations with greater efficiency and that, for a given fruit sample, the natural or resonant frequency decreases as the fruit matures or begins to degrade.

It is also known that many fruits exhibit multiple natural frequencies and that only some of these frequencies contain information which relates to fruit texture, see: J. A. Abbott et al "Sonic Techniques for Measuring Texture of Fruits and Vegetables", Food Technol. 1968, 22 (5):101–112; E. E. Finney et al, 1978 "Methods for testing the dynamic mechanical response of solid foods", J. Food Quality 2:55-74, and; E. E. Finney, Jr. 1972, "Vibration Techniques for Testing Fruit Firmness", J. Texture Studies, 3:263-283. The prior art devices such as those described by: E. E. Finney, "Mechanical Resonance within Red Delicious Apples and Its Relation to Fruit Texture", Trans. ASAE, 1970, pages 177 to 180, H. L. Clark et al, 1942, "Fruit Ripeness Tester" U.S. Pat. No. 2,277,037, and J. A. Abbott et al 1968, Ibid; employ a frequency scanner to vibrate the object at a series of frequencies and query each frequency to detect the natural frequency for that sample. This method is time consuming and can be damaging to the fruit. Other devices excite the fruit (see e.g. D. R. Bower et al, "Application of Vibrational Sorting to Blueberry Firmness Separation", Trans. ASAE, 1976, pages 185-191) with a single frequency and determine how that sample's vibration compares with the calibration set. This method can be inaccurate if the fruit's mass or variety differs from that of the calibration set. Furthermore, the number of ripeness categories into which a fruit may be designated is highly limited by the single frequency method. Still other devices such as Abbott et al supra require that fruit be suspended in space by the stem end with vibrations probed about the fruit's equator. This method is time consuming, and the suspension is impractical for field operations. Furthermore, this method is highly sensitive to air currents and background vibrations in the environment.

It is also known from Finney 1970, supra, that devices used to couple vibrations from the vibration generator to the commodity must be capable of transmitting the vibrations without distortion. Prior art devices have employed rigid frames for this purpose which damage fruit and do not reliably excite the same resonant modes of vibration in consecutive samples, thus promoting improper classification of the fruit.

The present invention takes advantage of the fact that, as agricultural commodities mature, internal changes take place in regard to the rigidity of the cell walls, the stiffness of the cell walls and intercellular bonding agents, the turgor pressure within the cells and the size of intercellular air spaces. Furthermore, as these changes occur during maturation or degradation, the elastic nature of the agricultural commodity will change. Mechanical, high frequency vibrations are transmitted more efficiently through a less elastic material. A less elastic material will also develop its own natural vibrations at higher frequencies when excited. A sonic impulse containing regulated frequencies can be passed through an agricultural commodity to excite and identify these natural vibrations as a measure of the internal condition (i.e. texture, maturity and extent of damage (if any)) of the whole agricultural commodity. This method of analysis provides a full spectrum of sonic wave energy that has passed through the agricultural commodity, which can then be classified according to a set of calibrated samples. The output is a measure of the internal condition of the whole agricultural commodity. Utilization of the condition measurement of the present invention may reduce agricultural commodity loss and increase net return by providing an objective measure upon which to channel product flow to the market where it may be utilized most efficiently and economically. For example, in 1988, the United States produced 192 million bushels of apples, of which 111 million were marketed fresh and 80 million were processed. Another half million were not marketed. Greater returns can result when losses are reduced and specific levels of consumer quality can be guaranteed, particularly in the dominant fresh market. Furthermore, producers can benefit from early evaluation of harvest quality.

SUMMARY OF THE INVENTION

It is an object of the present invention to provide new and improved methods and apparatuses for use in non-destructively determining the condition of agricultural commodities.

A further object is the provision of an improved method of vibration in which the excitation includes a band-limited (frequency compressed) impulse.

Another object is to provide vibration of the above character in which the amplitude and frequency of the frequency band can be quickly and easily modified for different types of agricultural commodities.

Another object is to provide a vibration impulse (of the above character) which is extremely short in duration (e.g. less than 1 second) and small in magnitude, thus eliminating potential damage to the agricultural commodity (AC) and providing a capability for high throughput of measurement samples.

Another object is to provide an agricultural commodity retaining means which is not sensitive to air currents.

Another object is to provide an AC support means which facilitates ready measurement of optical properties of the AC, as for example by presenting more than 90% of the AC surface to an optical inspection system, thereby permitting incorporation of color, shape, surface abnormalities, surface features and size measurements into the system for classification.

Another object is to provide a sample support means which permits incorporation of size measurements (e.g. mass, diameter and/or volume) into the system for classification.

Another object is to provide a nondestructive condition measurement method and apparatus which is not adversely affected by small background vibrations in the environment.

Another object is to provide a conforming (non-rigid) coupling medium that transmits band-limited vibrations without distortion or with known distortion (which may be compensated for or used as a reference in the final measurements) from the vibration source to the AC.

Another object is to provide a coupling medium of the above character which requires no attachment, bonding or precise alignment to the agricultural commodity.

Another object is to provide a coupling medium of the above character which contacts a sufficient surface of the commodity, such that potential damage to the commodity is eliminated and similar vibration modes are induced in each measured sample (commodity).

Another object is to provide improved vibration detection capable of high-precision, and low level vibration sensing, which requires no attachment or bonding to the commodity.

Another object is to provide an analysis means in which the vibration amplitude in a given frequency band can be evaluated in the time domain using software filtering.

Another object is to provide an improved analysis means in which the time domain vibration signal can be converted to the frequency domain (e.g. using the Fourier Transform algorithm, or the like) and subsequently characterizing AC condition by the resonance frequencies exhibited or functions thereof.

Still another object is to provide nondestructive condition measurement of the above character which: has improved commodity classification capability, eliminates potentially damaging vibration coupling, and provides higher speed, accuracy and adaptability of vibration excitation and measurement.

Still another object is to provide nondestructive condition measurement of the above character which can classify damaged agricultural commodities from undamaged agricultural commodities, such as classifying punctured, bruised and/or decayed agricultural commodities from unpunctured, unbruised and/or undecayed agricultural commodities.

The aforementioned objects and advantages of the instant invention (as well as other objects and advantages which will become readily apparent from the ensuing description) may be accomplished either singularly or additively, and the aforementioned drawbacks of the prior art may be avoided, by processes or apparatuses, for measurement of the condition (i.e. texture, maturity and extent of damage (if any)) of an AC, relating to: vibrating an AC with input vibrations which comprise a band-limited range of simultaneous input frequencies (i.e. limited to a specific frequency band) of from about 1 to about 3,000 Hz; sensing vibrational characteristics of vibrations of the AC resulting from the input vibrations and analyzing either: (a) vibrational energy at single frequencies or within a frequency band, or (b) resonance and absorption frequency characteristics; in order to ascertain the condition of said agricultural commodity.

DETAILED DESCRIPTION OF THE PREFERRED EMBODIMENTS

For purposes of the present invention the term "condition" is intended to refer to texture, maturity and extent of damage (if any).

Figure 1:
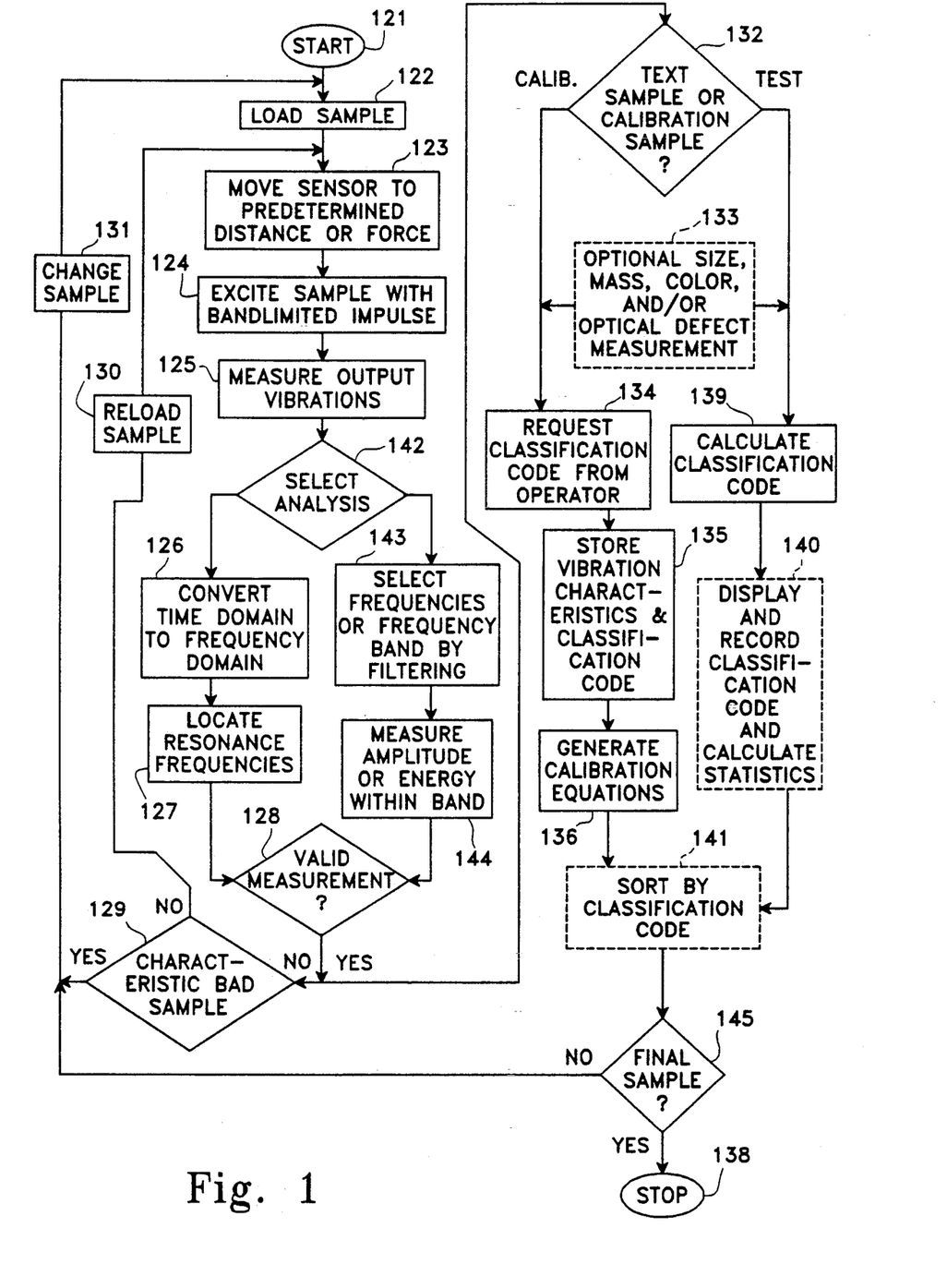
FIG. 1 is a flow chart depicting an embodiment of the present invention.
Figure 2:
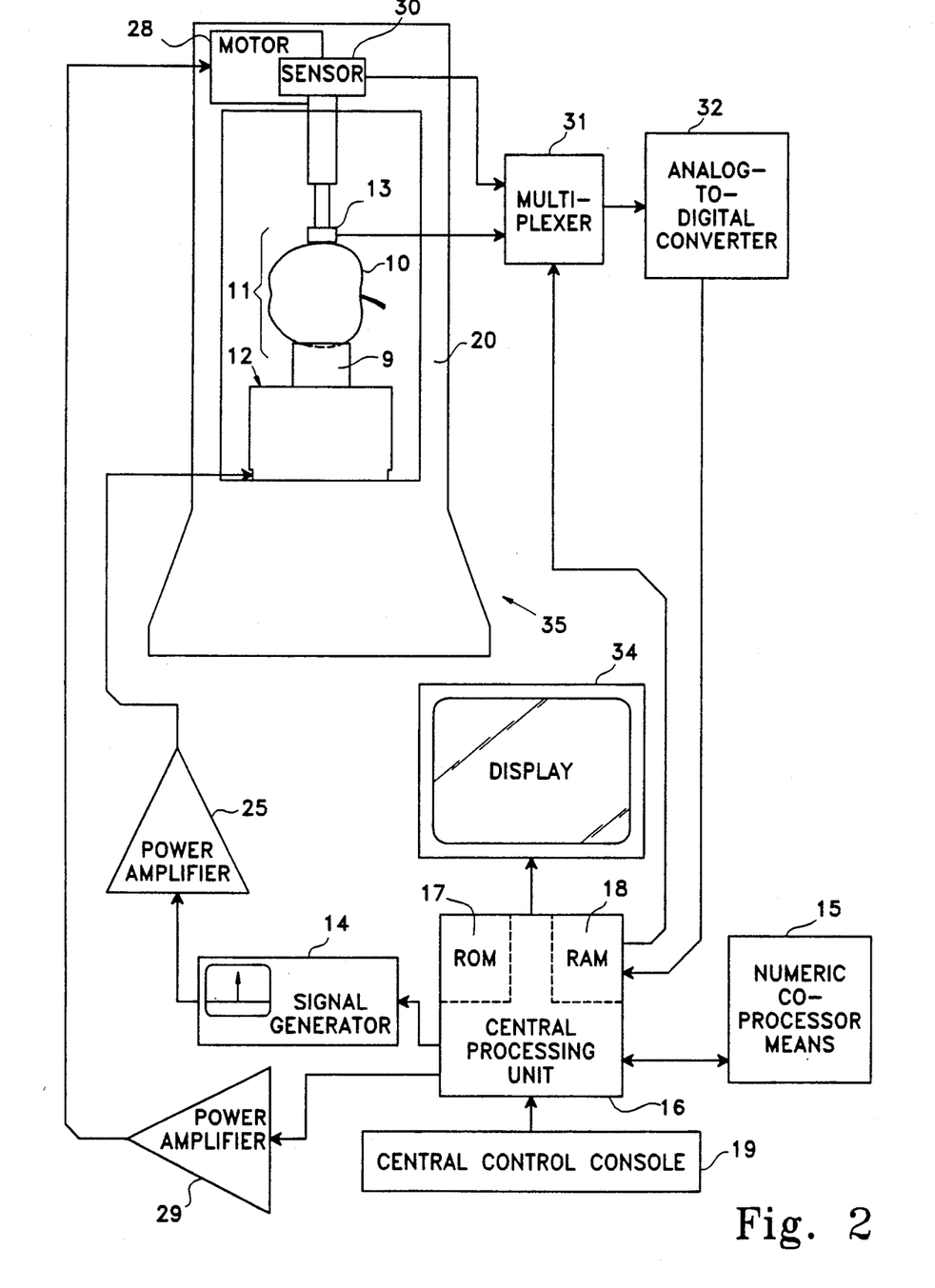
FIG. 2 is a functional schematic of a device of the present invention.

Referring to FIG. 1, there is shown a flow chart illustrating an exemplary process of the present invention. FIG. 1 will be described in greater detail hereinafter in regard to the operation of the various devices of the present invention. FIG. 2 depicts a device of the present invention, including a frame 20 (which may be positioned atop a housing 35) having mounted thereon a vibration source (i.e. means for vibrating) designated 12 which functions to vibrate an agricultural commodity designated 10 (positioned in a measurement position 11) with input vibrations which comprise a band-limited range of simultaneous input frequencies of from about 1 to about 3,000 Hz. Examples of such a vibration source include Model V203 Electromagnetic Vibrator from Ling Dynamic Systems, Hartfordshire, England. In the context of the present invention the phrase "band-limited" refers to frequencies which are limited to a specific frequency band. It is preferred, where a variety of types of ACs are to be tested, to provide a vibration source which is adjustable as to its output frequency and/or amplitude range. It is also preferred that in order to save time, and prevent undesirable gross movement of the AC, the input vibrations be provided in the form of an impulse. While said agricultural commodity is shown for purposes of illustration as an apple, it should be understood that the present invention may be practiced with any of a variety of agricultural commodities including for example fruits and vegetables, such as, apple, pear, peach, tomato, watermelon, citrus fruits, lettuce, avocado, strawberry, blueberry, cabbage, potato, onion, turnip and carrot. The range of band-limited simultaneous input frequencies may be adjusted according to the type of agricultural commodity being tested. Exemplary frequency ranges for a number of specific ACs are illustrated in Table 1.

TABLE 1

| Agricultural Commodity | Frequency Range (Hz) |
| --- | --- |
| Apple | 50 to 2,500 |
| Peach | 40 to 1,000 |
| Pear | 50 to 1,000 |
| Orange | 60 to 700 |
| Lettuce | 20 to 300 |
| Potato | 50 to 500 |

Figure 7A:
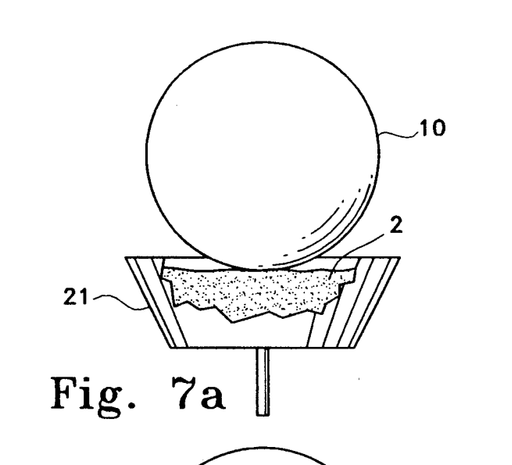
FIGS. 7a, 7b, 7c and 7d are alternative means for retaining an agricultural commodity (AC).
Figure 7B:
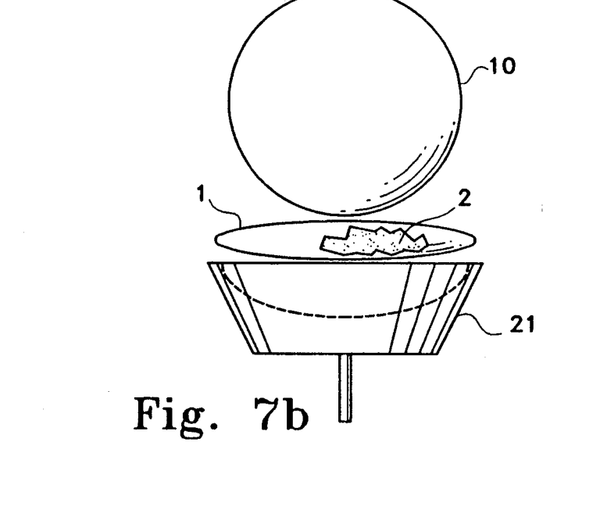
Figure 7C:
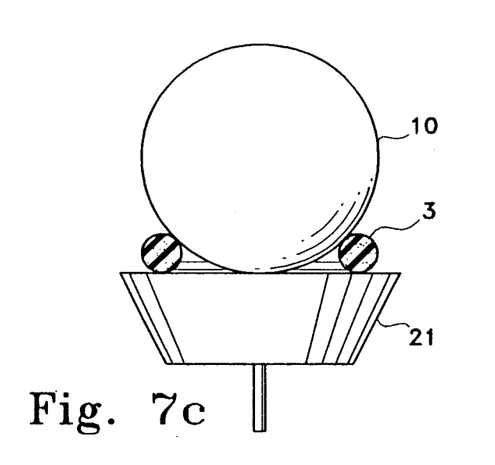
Figure 7D:
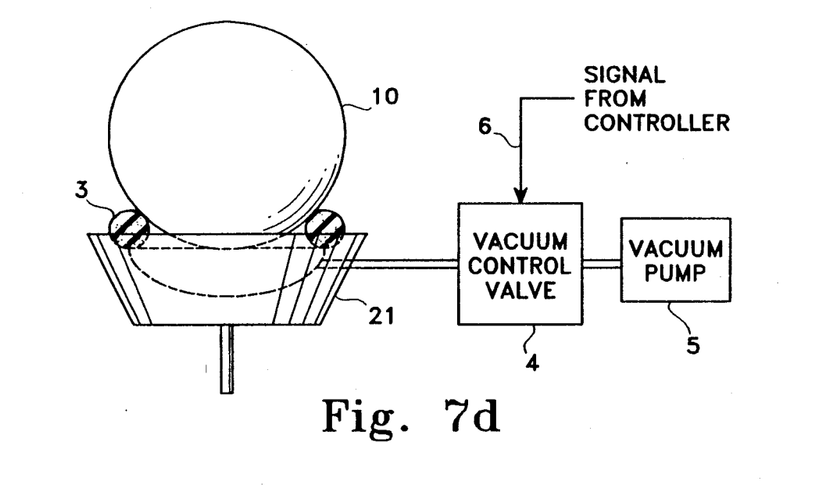

Narrower bands within these ranges may be satisfactory for some applications or commodities. One of ordinary skill, after having reviewed the instant disclosure, may select an appropriate frequency range (within the aforementioned range of about 1 to about 3,000 Hz) for each type of AC and may adjust the input frequency range accordingly. The device of FIG. 2 may optionally also include means for retaining an agricultural commodity designated 9. Said means 9 should be constructed so as to transmit vibrations from said vibration source 12 to said agricultural commodity 10, and may be configured in any of a variety of said shapes and sizes depending upon the size and shape of the agricultural commodity to be tested. It has surprisingly and unexpectedly been discovered that structures suitable for said retaining means 9 includes those structures illustrated in FIG. 7. As shown in FIG. 7a an open top container (e.g. cup or pan) 21 may be utilized to retain therein a material designated 2 which is: (a) a deformable material, such as one or more of rubber, sponge or plastic, and/or; (b) a fine granular material such as one or more of sand, glass beads, salt, clay (e.g. floral clay), and/or; (c) a gel or imcompressible fluid (e.g. oil, water); with a sample designated 10 placed on top of said material 2. Alternatively, as shown in FIG. 7b the sample 10 may be placed on a flexible bladder or bag or envelope designated 1 (which may for example be composed on plastic or rubber) retaining therein one or more of the aforementioned materials 2. The flexible bladder 1 is placed on top of the container 21. A third alternative structure is illustrated in FIGS. 7c and 7d, wherein the sample 10 is supported on an annular ring 3 (e.g. of rubber or sponge or other deformable material) which is in turn supported by the container 21. Additionally, with the embodiments of FIGS. 7c and 7d, means for producing a vacuum as illustrated in FIG. 7d may be provided in order to draw the sample 10 against the ring 3 and thus securely hold the sample to the means for retaining the AC. The means for producing a vacuum may for example include a vacuum pump 5 which is connected via tubes/pipes and vacuum control valve 4 to the interior of container 21. The pump 5 functions to draw a partial vacuum on the lower portion of the AC 10, on the ring 3 and in the interior of container 21; and thus pulls the AC 10 securely against the ring 3, and thereby holds the AC 10 securely during testing. Signals designated 6 are sent from the controller to the vacuum control valve so that the vacuum is applied before and during testing and the vacuum is released when the AC is to be released from the means for retaining.

Returning to FIG. 2, there is also shown therein a vibration sensor (i.e. means for sensing) 13. The sensor should be of small mass in comparison to the AC so that the sensor does not interfere with the vibration of the AC.

Examples of vibration sensors which may be utilized in the present invention include: (1) a piezoelectric sensor e.g. a piezoelectric accelerometer such as a Model No. 2222 from Endevco Corp., Pasadena, CA; (2) electromagnetic sensors such as a Model No. 33-2011 condenser microphone from Radio Shack, Fort Worth, Tex. (such sensors need not be in contact with the AC), or; (3) an optical sensor (which optionally may also sense AC shape, surface features, color, surface abnormalities and/or volume), such as the Opcon Vision System from Design Systems Inc., Kent, Wash. Sensors which do not contact the AC have the advantage of avoiding any interference with vibration of the AC.

FIG. 2 depicts the sensor 13 lowered into contact with the agricultural commodity and thus in position to sense vibrational characteristics of vibrations of said agricultural commodity resulting from the input vibrations. The phrase "vibrational characteristics" is intended to refer to: vibrational energy, vibrational frequencies, resonance and absorption frequency characteristics, amplitudes and phases. Means are provided for lowering the sensor 13 into the proximity of, or into contact with, the agricultural commodity, and for raising the sensor 13 in order to permit the agricultural commodity to be removed from the device. Said means may for example take the form of a bi-directional motor 28 (mounted on frame 20) which receives control signals from a central processing unit (CPU) 16 (which includes read-only memory (ROM) 17 and random-access-memory (RAM) 18) via a power amplifier 29. The CPU may be any well known commercially available central processing unit chip, which preferably operates at 10 MHz or more, such as a Model No. 6800 L10 from Motorola Corp., Phoenix, Ariz. Program information may be stored in ROM 17, while calibration values may be entered through console 19 and stored in RAM 18 during operation, thus the CPU may function as an analyzing means (e.g. analyzing vibrational energy of the vibrations of the AC at single frequencies or within a frequency band, and analyzing resonance and absorption frequency characteristics) to ascertain the condition of the AC. The aforementioned amplifier 29 may be any suitable electrical amplifier such as a Darlington pair configuration or an E-350M from Electro Craft Corp., Hopkins, Minn. The position of sensor 13 may be sensed by a force or position sensor means 30. Examples of force sensor means which may be utilized in the present invention include a Model No. 2103-100 force gauge from Endevco Corp., Pasadena, Calif., and examples of such position sensor means include a Model No. H25 optical encoder from BEI Motion Systems, Inc., Goleta, Calif. While for purposes of illustration the vibration source 12 and vibration sensor 13 are shown in the drawings as being on opposite sides of the agricultural commodity; in fact, these elements do not need to be on opposite sides of the agricultural commodity. A first signal from said sensor 30 (indicative of the position of sensor 13) and a second signal from the sensor 13 (indicative of the vibrational characteristics of the agricultural commodity) are both transmitted to multiplexer 31 (which may for example be a SN74AS851 from Texas Instruments, Dallas, Tex.) for switching between sensor signals and (if necessary) subsequently transmitting signals to an analog-to-digital converter 32 (e.g. a Model No. LF 13300 from National Semiconductor, Santa Clara, Calif.) for conversion from an analog signal to a digital signal, and ultimately to the random access memory (RAM) 18 of central processing unit 16 for use in controlling the motor 28. Also, said multiplexer 31 receives a switching signal from the RAM 18 of CPU 16 to select the desired sensor to read. The device of FIG. 2 is controlled from a central control console (CCC) 19 which may for example include an alphanumeric keyboard and encoder such as an MM5740 Keyboard Encoder from National Semiconductor, Santa Clara, Calif. When it is desired to test an agricultural commodity, a command is transmitted from the CCC 19 which triggers CPU 16 to activate signal generator 14 to provide a bandlimited impulse to vibration source 12 via power amplifier 25. Such a signal generator may for example be a Model No. 8904A from Hewlett Packard Corp., Rockville, Md. Examples of suitable power amplifiers include Model No. N-100 available from Electrodyne Corp., Alexandria, Va. In some applications or embodiments of the instant invention, it may be desired to convert signals from 13 from time-domain to frequency domain. The CPU 16 sends signals indicative of the sensed vibrations to a numeric co-processor means (NCM) 15 for conversion from time-domain to frequency-domain. Examples of NCM which may be utilized in practicing the present invention include a Model APS P-2100 from Analog Devices, Inc., Norwood, Mass. The converted signals are subsequently sent from NCM 15 to the CPU 16. The CPU 16 then locates resonance frequencies using e.g. a peak seeking routine. The device of FIG. 2 may also be provided with a suitable output device(s), such as a video display 34 which may for example be a HP1182A Color Video Graphics Display from Hewlett Packard Co., Rockville, Md.

Figure 3:
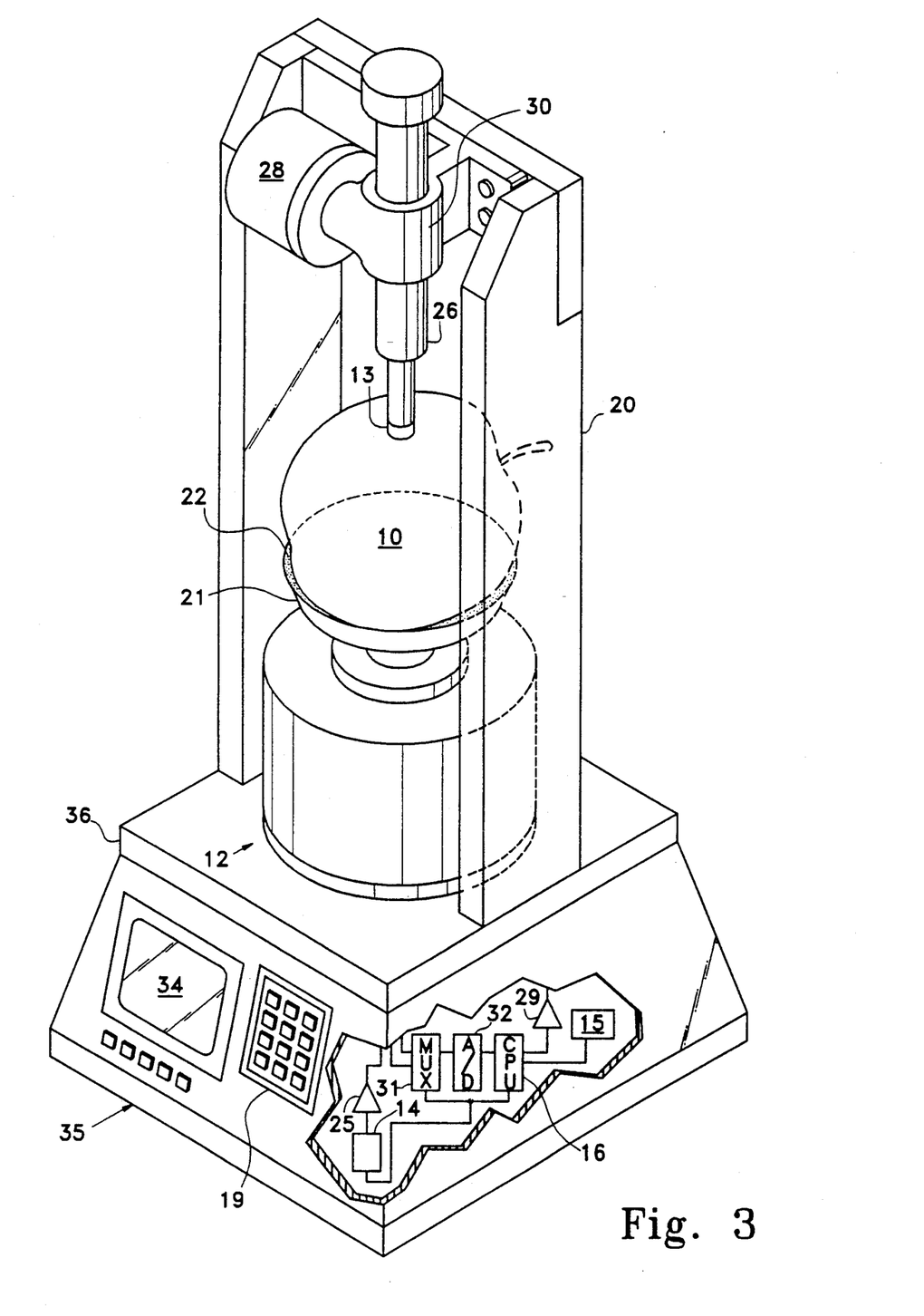
FIG. 3 is a perspective side view of a device of the present invention.

The embodiment of the present invention shown in FIG. 3 is basically similar to that of instant FIG. 2, with like elements being designated with the same numeral. FIG. 3 illustrates another embodiment of the means for retaining an agricultural commodity 10, by showing a container 21 in which is placed one or more of the aforementioned fine granular materials designated 22. The agricultural commodity is placed on top of said fine granular material. Also illustrated in FIG. 3 is protective shielding 36 which functions to shield the electronic components from the vibration source 12.

Figure 4:
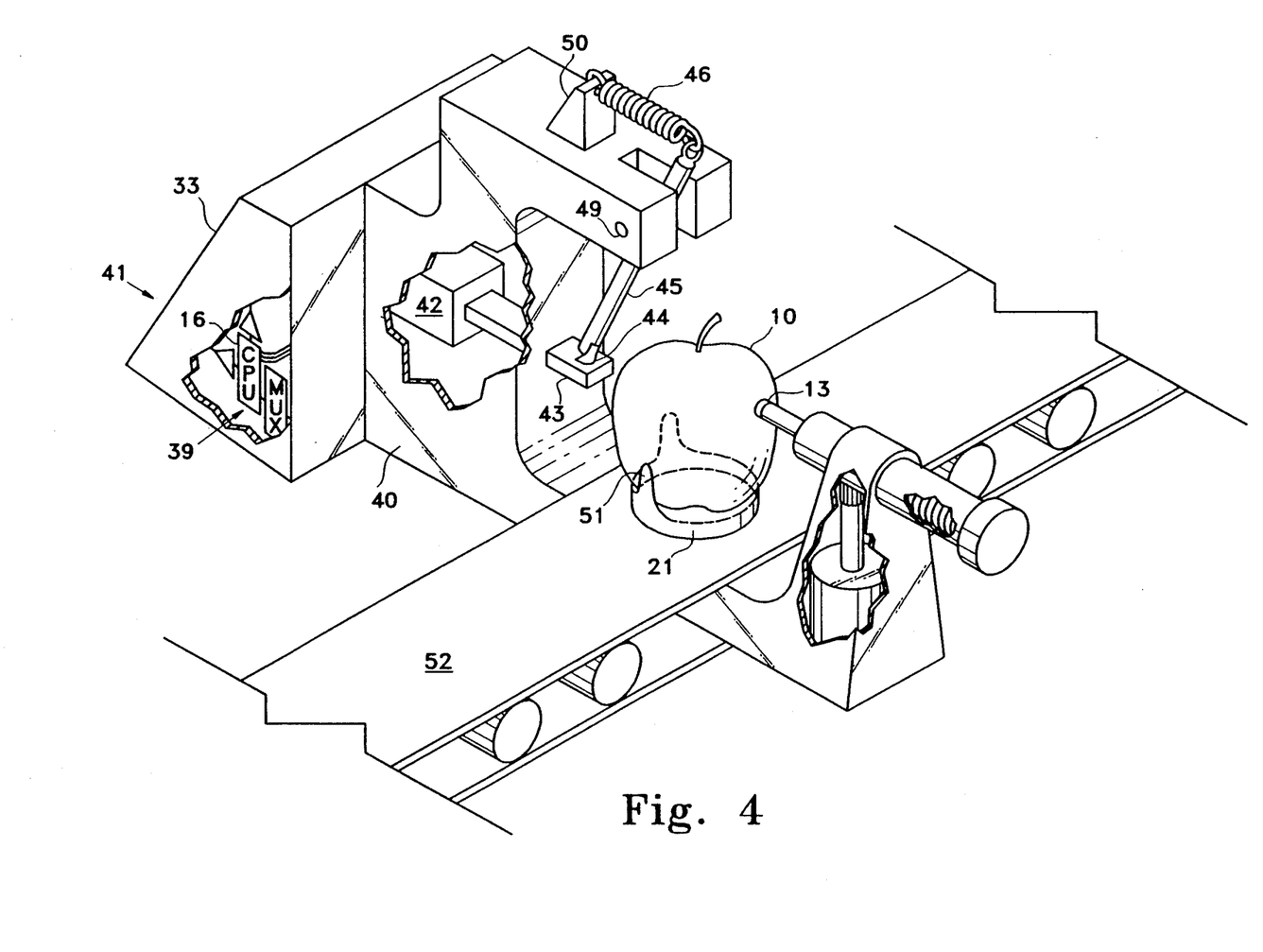
FIG. 4 is a perspective view of a further embodiment of the present invention.

FIG. 4 illustrates another embodiment of the present invention. The device shown in FIG. 4 includes a frame 40 carrying thereon a console 33, video display 34 and electronics package 39 inside a housing 41. An electromagnet 42 controls motion of an arm 43 having thereon a tab 44. The tab temporarily restrains a lever 45 (impact means) which is pivotally mounted on a pin 49. Tension spring 46 is attached at one of its ends to block 50 and at its other end to lever 45. Thus spring 46 urges lever 45 toward each agricultural commodity 10, and provides for impacting the AC with the lever (impact means). The device of FIG. 4 is suitable for rapid and convenient testing of a plurality of agricultural commodities by virtue of the provision of a plurality of containers 21 attached at regular intervals to a conveyor (e.g. endless belt conveyor) 52. For ease of illustration only one such container is shown in FIG. 4. The container 21 may be provided with one or more support arms 51, to aid in retaining the agricultural commodity when it is contacted by the lever 45 and vibration sensor 13. In operation, the CPU 16 energizes the electromagnet 42 thereby retracting arm 43 and releasing lever 45 from tab 44 (by virtue of the geometry of the arm, lever and tab) and permitting spring 46 to rapidly urge lever 45 into contact with the agricultural commodity, thus imparting limited vibrations to the agricultural commodity. The material of the lever must be capable of generating vibrations in the desired band. It is preferred to utilize wood or plastic to provide suitable vibrations and reproducibility. The lever should be configured to provide sufficient area of contact with the AC, to provide sufficient vibrational input while not damaging the AC.

Figure 5:
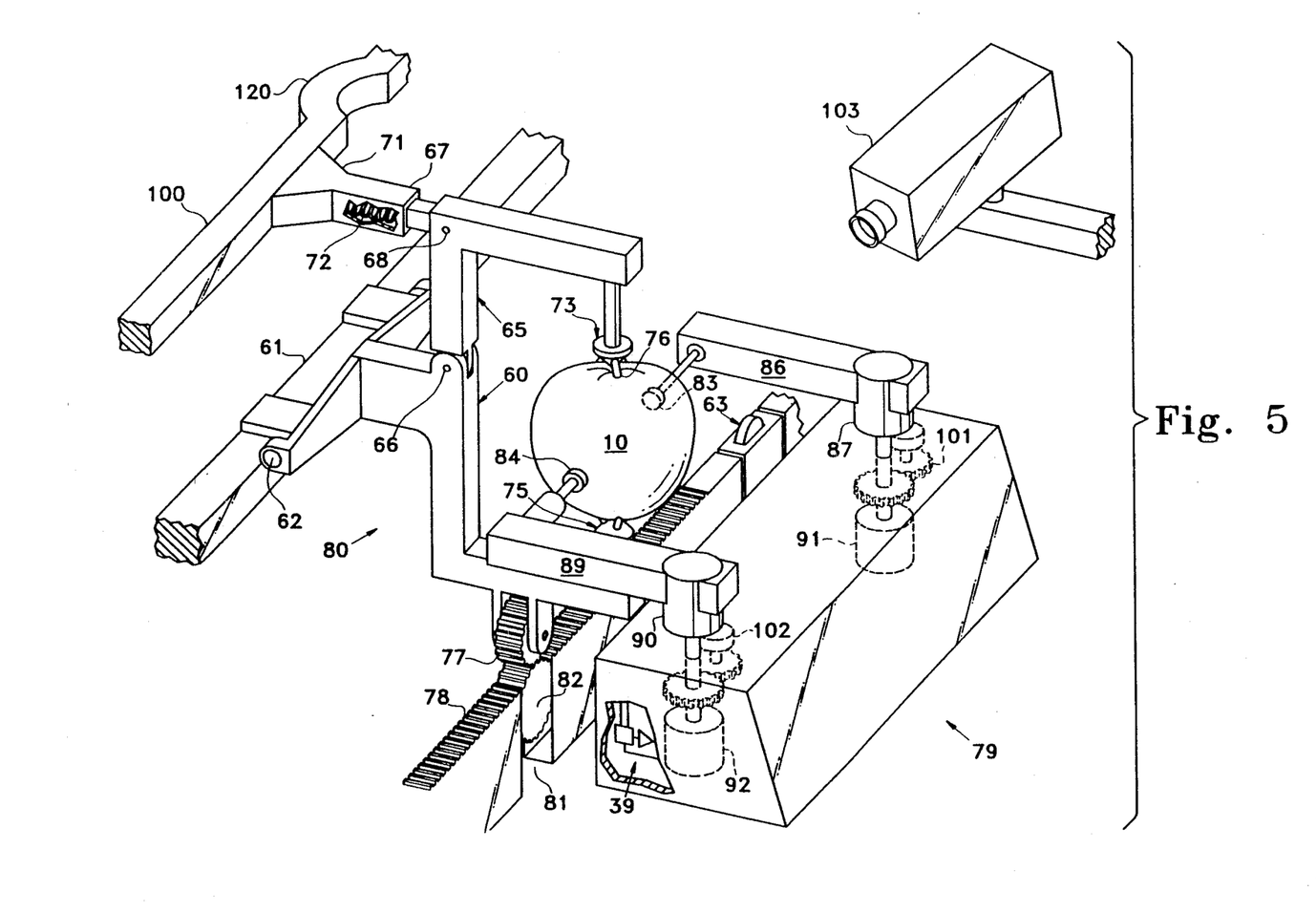
FIG. 5 is a perspective view of an alternative embodiment of the present invention.

Turning now to FIG. 5 there is shown a device of the present invention which provides rapid and convenient measurement of several agricultural commodity characteristics (e.g. mass, diameter, volume, shape, surface features, color, surface abnormalities, as well as vibrational characteristics), all of which may be considered in ascertaining AC condition. Said device includes a sample transport generally designated 80, which includes a lower frame 60 and an upper frame 65. Lower frame 60 is pivotally mounted to track 61 via pin 62. Upper frame 65 is: (1) pivotably attached at a lower end thereof to the upper end of lower frame 60 by means of a pin 66, and; (2) pivotably attached to a slider arm 67 by means of a pin 68. An optional rotary displacement sensor (which may for example be a Model No. H25 optical Encoder from BEI Motion Systems, Co., Goleta, Calif.) at pin 66 can provide longitudinal diameter measurements to electronics package 39 (via means for communicating such measurements from such a size measuring means to analyzing means) for inclusion in ascertaining AC condition. Slider arm 67 is fixed to internal spring 72 in track mount 71 to provide compression on upper frame 65, thus holding upper sample grip 73 firmly against agricultural commodity 10. Upper sample grip 73 is rotatably mounted to upper frame 65 and is free to spin with lower sample grip 75. Both upper and lower grips 73 and 75 are equipped with fingers 76 to prevent slippage of agricultural commodity 10. The design of transport 80 also permits use of additional optical and/or mechanical sensing means (such as a camera designated 103 in FIG. 5, which may for example be a CCD camera from COHU Corp, San Diego, Calif.) for sensing shape, color, size (e.g. volume or diameter), surface characteristics, and/or surface defects.

The mass of the agricultural commodity 10 may be measured by placing the transport 80 holding the agricultural commodity 10 upon a scale 63 (i.e. mass measurement means, which may for example be a Model No. 2103-100 Force Gauge from Endevco Co., Pasadena, Calif.), making a measurement with scale 63, and then subtracting the mass of the transport 80 from the mass measurement made by the scale 63. The transport 80 and agricultural commodity 10 may be placed upon the scale 63 by use of a drive wheel 77 rotatably attached to a lower portion of lower frame 60. The drive wheel 77 is rotated, and by engagement (e.g. frictional or by means of gears) with track 78 moves the transport 80 holding the agricultural commodity to the right and rearwardly as viewed in FIG. 5. When the transport and agricultural commodity are moved onto scale 63, a bend 120 in track 100 releases the compression from spring 72 on upper frame 65, thus providing a valid mass measurement of the transport and sample without interference from the spring force. Drive wheel 77 is internally geared to lower sample grip 75 thereby providing rotation of agricultural commodity 10 for seating of sensors. Track 78 is stationary, and defines a gap 81 in front of texture measuring station 79. In gap 81 is a large gear 82 which is controlled by electronics package 39 inside console 19 and which mates with drive wheel 77 to cause rotation of agricultural commodity 10 while transport 80 is stationary over the gap. Rotation is employed to adjust seating of vibration sensor 83 and vibration source 84 onto the agricultural commodity. Such a vibration sensor may for example be a 2222 piezoelectric Vibration Sensor from Endevco Corp., Pasadena, Calif. Such a vibration source may for example be a bidirectional electromagnetic solenoid from Ling Dynamic Systems, Hartfordshire, England. The vibration sensor 83 is fixed to one end of an arm 86, which is in turn rigidly mounted to a vertical shaft 87. Vibration source 84 is fixed to an arm 89, which is in turn rigidly mounted on a vertical shaft 90. Both shafts 87 and 90 are rotatably mounted to station 79 and pivot so as to bring the sensor and exciter into contact with agricultural commodity 10 when transport 80 stops in front of the console. Shafts 87 and 90 are controlled by drive motors 91 and 92, (which may for example be an E586 motor-tach from Electro-Craft Corp., Hopkins, Minn.), which in turn, are operated by electronics package 39. Position or force sensors 101 and 102 (such as, a L25 encoder available from BEI Motion Systems Co., Goleta, Calif., or a force sensor available from Sensym Co., Sunnydale, Calif.) attached to shafts 87 and 90 provide feedback to properly locate sensor 83 and source 84 in proximity to agricultural commodity 10. The sensors 101 and 102 may optionally provide an equatorial diameter measurement to electronics package 39 for inclusion in ascertaining texture. The volume of the AC may be measured by: use of the camera 103 to sense shape of the AC; use of the camera or mechanical means to sense AC diameter, length, height, etc.; and use of geometric formulas (e.g. related to shapes such as a sphere or ellipsoid) to estimate AC volume.

Figure 8:
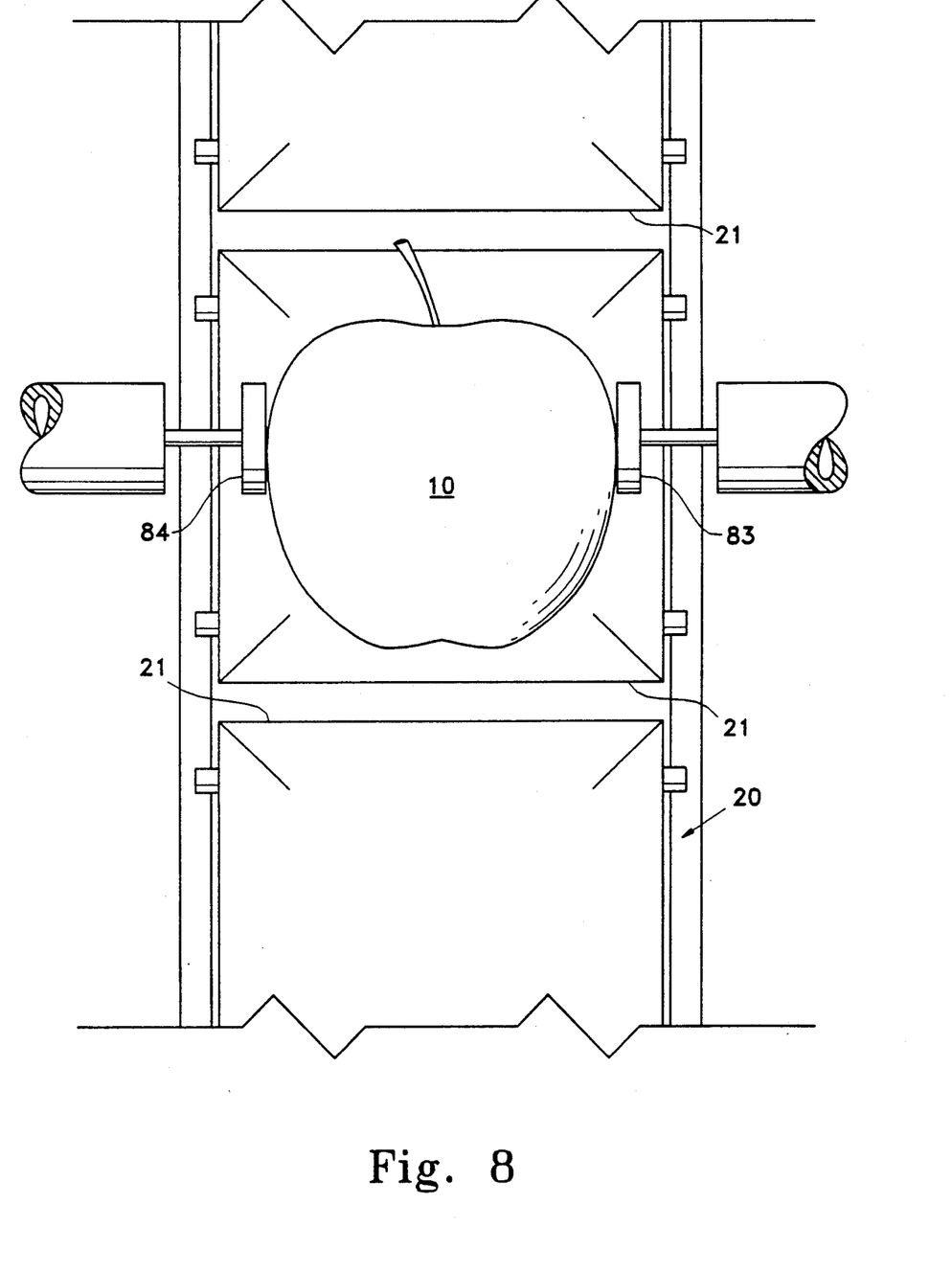
FIG. 8 shows means for practicing the present invention with ACs carried on a conveyor of the type now used for sizing ACs.

FIG. 8 discloses an embodiment of the present invention generally analogous to that of FIG. 5, except that in FIG. 8 a conveyor (including containers 21 and a frame 20) is employed which is of a type now in use for sizing fruit. The vibration sensor 83 and vibration source 84 of the present invention, as referred to herein above, are placed on either side of the conveyor. The instrumentation and controls as described in connection with FIGS. 4 and 5 may be utilized in the embodiment of FIG. 8.

Figure 6:
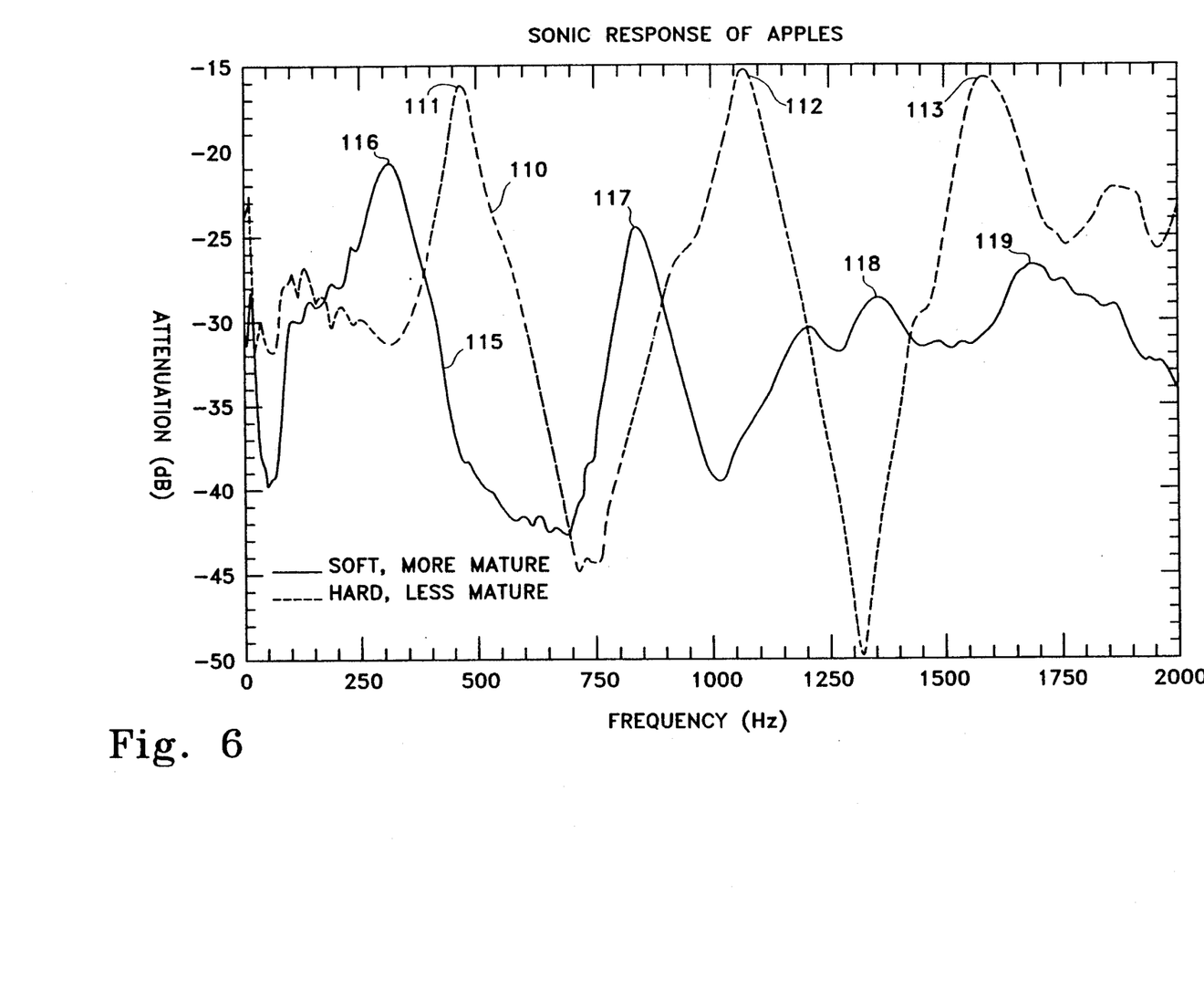
FIG. 6 is a graph of frequency transmission curves and resonant frequency identification (i.e. attenuation in decibels vs. frequency in Hz) for two apples of different condition.

Referring now to FIG. 6, the response of apples to the methods and apparatuses of the present invention may be seen. Dashed trace 110 shows a frequency history of the response of a harder, less mature apple with resonant peaks 111, 112 and 113 identified. Trace 110 also exhibits little attenuation at peak 113, indicative of an undamaged sample. Trace 115 shows a similar frequency history of the response of a softer, more mature apple with resonant peaks 116, 117, 118 and 119 identified. The resonance at lower frequencies of trace 115, combined with the greater attenuation of transmitted energy at peaks 118 and 119 are indicative of the texture difference between these samples. Large attenuations occurring beyond the first resonance peak are indicative of a damaged or degraded specimen. Therefore, with the method of the present invention, some species of damaged samples can be identified.

The general method of use of the aforementioned devices will now be described in connection with FIG. 1. The process begins at start 121 and with loading a sample (i.e. agricultural commodity) at step 122. Subsequently, the vibration sensor is moved either a predetermined distance or at a predetermined force into contact with the agricultural commodity at step 123. Optionally, the vibration source may also be moved into contact with the agricultural commodity at this point. Next the vibration source or impact lever is activated to vibrate the agricultural commodity with a bandlimited impulse at 124, and output vibrations are measured/sensed by the vibration sensor at step 125. At step 142 the method of analysis is selected. If steps 126 and 127 are selected, than at step 126 the output is optionally converted from the time domain to the frequency domain by means of a Fourier algorithm operating in a dedicated microchip, or in the CPU, and the resonance frequencies are located with a peak seeking routine in the CPU in step 127. If steps 143 and 142 are selected, then the process procedes to select frequencies or frequency band by filtering at step 143 and measuring amplitude or energy within band at step 144. The data is evaluated at step 128 by the CPU to determine whether or not the measurement is valid. For example, a lack of peaks, very little vibration energy, or large attenuation beyond the first peak, are indications of an invalid measurement. If the measurement is determined not to be valid, then the process proceeds to step 129. Optionally, the amplitude or energy of a single frequency or band of frequencies is analyzed. If the amplitude or energy is lower or higher than predetermined values the measurement is considered invalid. In step 129, if the sample is determined to be bad (e.g. by large attenuation beyond the first peak) then there is a need to change samples (as indicated at 131) and the process recycles to sample loading step 122. If in step 129 the sample is not bad (i.e. the measurement rather than the sample appears to be improper, which may for example be indicated by a lack of peaks, or very little vibration energy) then the sample is reloaded in step 130, and the process returns to step 123. If in step 128 the measurement is determined to be valid then the process proceeds in one of two directions from step 132 depending on whether the agricultural commodity is a sample to be tested or to be used for calibration. If the agricultural commodity is to be used for calibration then, optionally size (e.g. mass, diameter and/or volume) is measured (step 133), and a texture value is requested from an operator. The operator responds by inputting a classification code (which may relate to firmness, damage, or point of disposition). The CPU is programmed to store vibration characteristics and classification codes (step 135), as calibration values to be used in subsequent testing. In step 136, the CPU uses the stored information to generate calibration equations. Alternatively, at step 132, if the agricultural commodity is a sample to be tested, then the process proceeds to optional step 133 of measuring size. Subsequently, at step 139 a condition value (i.e. classification code) is calculated according to the equation $$\text{classification code} = K \cdot V^x \cdot S^y + C + ZP^A$$

where:
V = a numerical value related to the vibration characteristics (amplitude, frequency and/or phase)
S = a numerical value related to the size of the A.C. (which may be a function of mass, diameter and/or volume)
P = a numerical value related to the optical characteristics (e.g. shape, surface features, color and/or surface abnormalities)

and A, K, X, Y, Z and C are constants determined by regression analysis during the calibration phase. Thus, in utilization of the aforementioned equation, one or more size characteristics and/or one or more optical characteristics may be incorporated into the calculation (i.e. ascertaining) of the condition of the AC. Optionally the classification code for the sample may be displayed at step 140. Subsequently either step 136, 139 or 140 may be followed by an automatic sort according to the classification as indicated at 141. If this is the final sample to be evaluated then at step 145 the process proceeds to step 138. Alternatively, if it is not the final sample, then at step 145 the process proceeds to step 131 and the process is repeated for the next sample. Thus the present invention may be utilized to control a conventional automatic AC sorter to automatically sort a plurality of ACs of a single type of AC according to their condition, or to indicate to human sorters the condition of the AC (i.e. how it should be manually sorted). Thus in those instances when automatic sorting is utilized, means are provided for sorting ACs of a single type of AC according to condition ascertained by the analyzing means, and means are provided for communicating the condition from the analyzing means to the means for sorting. The process may then stop at step 138, or repeat the process (or portions thereof) for the next sample.

It is contemplated that the measurements of the present invention may be performed at any of numerous stages of handling the agricultural commodities, e.g., where the agricultural commodity is grown, in combination with harvesting the agricultural commodity, at a packing house, point of shipment, point of storage, point of wholesale distribution to determine where the agricultural commodities may best be utilized (e.g. fresh market, processing, or storage), and at the point of retail sale. Another advantage of the present invention is that the aforementioned measurements may be utilized to increase uniformity of quality of agricultural commodities in a pack, thus providing packaged agricultural commodities of greater uniformity, and therefore desirability and value.

The foregoing detailed descriptions and examples are given merely for purposes of illustration. Modifications and variations may be made therein without departing from the spirit and scope of the invention which is defined by the appended claims.

INDEX OF ELEMENTS 1. flexible bladder
2. fine granular material, gel or incompressible fluid
3. ring
4. vacuum control valve
5. vacuum pump
6. signal from controller
9. means for retaining an agricultural commodity
10. agricultural commodity (AC)
11. measurement position
12. vibration source
13. vibration sensor
14. signal generator
15. numeric coprocessor means (NCM)
16. central processing unit (CPU)
17. read only memory (ROM)
18. random access memory (RAM)
19. central control console (CCC)
20. frame
21. container
22. fine granular material, incompressible fluid, and/or gel
23. supporting conveyor track
24. support pins
25. power amplifier
26. spring loaded cylinder
28. bidirection motor
29. amplifier
30. sensor means
31. multiplexer
32. analog-to-digital converter
33. console
34. video display
35. housing
36. protective shielding
39. electronics package
40. frame
41. housing
42. electromagnet

INDEX OF ELEMENTS -continued 43. arm
44. tab
45. lever
46. tension spring
49. pin
50. block
51. support arms
52. conveyor
60. lower frame
61. track
62. pin
63. scale
65. upper frame
66. pin
67. slider arm
68. pin
71. track mount
72. internal spring
73. upper sample grip
75. lower sample grip
76. fingers
77. drive wheel
78. track
79. texture measuring station
80. sample transport
81. track gap
82. gear
83. vibration sensor
84. vibration source
86. arm
87. shaft
89. arm
90. shaft
91. drive motor
92. drive motor
100. track
101. position/force sensor
102. position/force sensor
103. camera
110. hard apple trace
111. resonant peak
112. resonant peak
113. resonant peak
115. soft apple trace
116. resonant peak
117. resonant peak
118. resonant peak
119. resonant peak
120. track bend

We claim:

1. A process for measuring the condition of an agricultural commodity comprising:
   vibrating an agricultural commodity with input vibrations which comprise a band-limited impulse generating a range of simultaneous, regulated input frequencies of from about 1 to about 3,000 Hz,
   sensing vibrational characteristics of vibrations of said agricultural commodity resulting from said input vibrations, and
   analyzing vibrational energy of said vibrations of said agricultural commodity at single frequencies or within a frequency band in order to ascertain the condition of said agricultural commodity.

2. The process of claim 1 wherein said step of sensing includes sensing resonance and absorption frequency characteristics of said agricultural commodity and, wherein said step of analyzing includes incorporating the detected resonance and absorption frequency characteristics into said ascertaining of the condition of said agricultural commodity.

3. A process for measuring the condition of an agricultural commodity comprising:

vibrating an agricultural commodity with input vibrations which comprise a band-limited impulse generating a range of simultaneous, regulated input frequencies of from about 1 to about 3,000 Hz, sensing resonance and absorption frequency characteristics of said agricultural commodity resulting from said input vibrations, and analyzing the sensed resonance and absorption frequency characteristics in order to ascertain the condition of said agricultural commodity.

4. The process of either claim 1, 2 or 3 further including:

measuring at least one size characteristics of the agricultural commodity selected from the group consisting of mass, diameter and volume; and wherein said step of analyzing includes incorporating said measurement into said ascertaining of the condition of said agricultural commodity.

5. The process of either claim 1, 2 or 3 further including:

measuring at least one of: shape, surface features, color and surface abnormalities of said agricultural commodity; and wherein said step of analyzing includes incorporating said measurement into said ascertaining of the condition of said agricultural commodity.

6. The process of either claim 1, 2 or 3 further including, conducting said steps of vibrating, sensing and analyzing for each of a plurality of agricultural commodities which are of a single type of agricultural commodity, and sorting said plurality of agricultural commodities according to said ascertained condition.

7. The process of either claim 1, 2 or 3 further including the step of transmitting said input vibrations to said agricultural commodity through a flexible bladder containing therein a material selected from the group consisting of: a fine granular material, an incompressible fluid, a gel, or mixtures thereof.

8. The process of either claim 1, 2 or 3 further including the step of transmitting said input vibrations through a material selected from the group consisting of: rubber, sponge, plastic, sand, glass, salt or clay.

9. The process of either claim 1, 2 or 3 wherein said step of vibrating includes striking said agricultural commodity with impact means.

10. An apparatus for measuring the condition of an agricultural commodity comprising:

means for vibrating an agricultural commodity with input vibrations which comprise a band-limited impulse generating a range of simultaneous, regulated input frequencies of from about 1 to about 3,000 Hz, operably associated means for sensing vibrational characteristics of vibrations of said agricultural commodity resulting from said input vibrations, and;

analyzing means, operably associated with said means for sensing, for analyzing vibrational energy of said vibrations of said agricultural commodity at single frequencies or within a frequency band in order to ascertain the condition of said agricultural commodity.

11. The apparatus of claim 10 wherein said means for sensing senses resonance and absorption frequency characteristics of said agricultural commodity, and wherein said analyzing means functions to incorporate the sensed resonance and absorption frequency characteristics into said ascertaining of the condition of said agricultural commodity.

12. An apparatus for measuring the condition of an agricultural commodity comprising:

means for vibrating an agricultural commodity with input vibrations which comprise a band-limited impulse generating a range of simultaneous, regulated input frequencies of from about 1 to about 3,000 Hz, operably associated means for sensing resonance and absorption frequency characteristics of said agricultural commodity resulting from said input vibrations, and;

analyzing means, operably associated with said means for sensing, for analyzing the sensed resonance and absorption frequency characteristics in order to ascertain the condition of said agricultural commodity.

13. The apparatus of either claim 10, 11 or 12 further including:

size measuring means for measuring at least one size characteristic of the agricultural commodity selected from the group consisting of mass, diameter and volume, means for communicating the measurement of at least one size characteristic from said size measuring means to said analyzing means, and wherein said analyzing means functions to incorporate the measurement of at least one size characteristic into said ascertaining of the condition of said agricultural commodity.

14. The apparatus of either claim 10, 11 or 12 further including:

measuring means for measuring at least one of: shape, surface features, color and surface abnormalities; of said agricultural commodity, means for communicating said at least one measurement from said measuring means to said analyzing means, and wherein said analyzing means functions to incorporate said at least one measurement into said ascertaining of the condition of said agricultural commodity.

15. The apparatus of either claim 10, 11, or 12 further including:

means for sorting agricultural commodities of a single type of agricultural commodity according to condition ascertained by said analyzing means, and means for communicating said ascertained condition from said analyzing means to said means for sorting.

16. The apparatus of either claim 10, 11 or 12 further including means for retaining said agricultural commodity and transmitting said input vibrations from said means for vibrating to said agricultural commodity.

17. The apparatus of claim 16 wherein said means for retaining said agricultural commodity and transmitting said input vibrations includes a flexible bladder containing therein a material selected from the group consisting of: a fine granular material, an incompressible fluid, a gel, or mixtures thereof.

18. The apparatus of claim 16 wherein said means for retaining said agricultural commodity is composed of at least one of: rubber, sponge, plastic, sand, glass, salt or clay.

19. The apparatus of claim 16 wherein said means for retaining said agricultural commodity includes means for producing a vacuum.

20. The apparatus of either claim 10, 11 or 12 wherein said means for vibrating includes, impact means, and means for impacting said agricultural commodity with said impact means.

* * * * *